United States Patent [19]
Strobl et al.

[11] Patent Number: 5,303,026
[45] Date of Patent: Apr. 12, 1994

[54] APPARATUS AND METHOD FOR SPECTROSCOPIC ANALYSIS OF SCATTERING MEDIA

[75] Inventors: Karlheinz Strobl, Los Angeles, Calif.; Irving J. Bigio, Los Alamos; Thomas R. Loree, Santa Fe, both of N. Mex.

[73] Assignee: The Regents of the University of California Los Alamos National Laboratory, Los Alamos, Calif.

[21] Appl. No.: 835,641

[22] Filed: Feb. 12, 1992

Related U.S. Application Data

[63] Continuation-in-part of Ser. No. 660,504, Feb. 26, 1991, abandoned.

[51] Int. Cl.$^5$ .............................................. G01N 21/63
[52] U.S. Cl. ................................ 356/318; 250/458.1; 128/665
[58] Field of Search .................. 356/73, 317, 318, 417; 250/458.1, 459.1, 461.1, 461.2; 128/395, 398, 665

[56] References Cited

U.S. PATENT DOCUMENTS

| | | | |
|---|---|---|---|
| 4,031,398 | 6/1977 | Callis et al. | 250/458.1 |
| 4,090,789 | 5/1978 | Macemon et al. | 356/318 |
| 4,718,417 | 1/1988 | Kittrel et al. | 606/15 |
| 4,930,516 | 6/1990 | Alfano et al. | 128/665 |
| 5,078,150 | 1/1992 | Hara et al. | 128/665 |

OTHER PUBLICATIONS

D. Kessel, "Tumor Localization and Photosensitization by Derivatives of Hematoporphyrin: A Review," IEEE J. Quantum Electron. QE-23, 1718 (1987).
R. Richards-Kortum et al., "Fluorescence Contour Mapping: Applications to Differentiation of Normal and Pathological Human Tissues," Program of the Conference on Lasers and Electro-Optics 1989, 1989 Technical Digest Series 11, 140.
I. M. Warner et al., "Multidimensional Luminescence Measurements," Analytical Chem. 57, 463A (1985).
I. M. Warner et al., "Design Considerations for a Two-Dimensional Rapid Scanning Fluorimeter," Analytica Chemica Acta 109, 361 (1979).
R. Richards-Kortum et al., "A Model for the Extraction of Diagnostic Information From Laser Induced Fluorescence Spectra of Human Artery Wall," Spectrochimica Acta 45A, 87 (1989).
R. M. Cothren et al., "Gastrointestinal Tissue Diagnosis By Laser-Induced Fluorescence Spectroscopy at Endoscopy," Gastrointestinal Endoscopy 36, 105 (1990).
R. R. Alfano et al., "Optical Spectroscopic Diagnosis of Cancer and Normal Breast Tissues," J. Opt. Soc. Am. B 6, 1015 (1989).
J. B. Zung et al., "Recent Developments and Applications of Multidimensional Fluorescence Spectroscopy," SPIE 1054, Proceedings of Fluorescence Detection III (1989), p. 69.
J. B. Zung et al., "Fiber Optic Based Multidimensional Fluorometer for Studies of Marine Pollutants," SPIE 990, Proceedings of Chemical, Biochemical, and Environmental Applications of Fibers (1988), p. 49.
J. B. Zung et al., "Design and Characterization of a Fiber Optic-Based Fluorimeter," Anal. Chim. Acta 224, 235 (1989).

*Primary Examiner*—F. L. Evans
*Attorney, Agent, or Firm*—Samuel M. Freund

[57] ABSTRACT

Apparatus and method for spectroscopic analysis of scattering media. Subtle differences in materials have been found to be detectable from plots of intensity as a function of wavelength of collected emitted and scattered light versus wavelength of excitation light.

7 Claims, 5 Drawing Sheets

APPARATUS AND METHOD FOR SPECTROSCOPIC ANALYSIS OF SCATTERING MEDIA

This is a continuation-in-part of copending application Ser. No. 07/660,504, filed on Feb. 26, 1991, now abandoned. The invention described herein is the result of a contract with the Department of Energy (Contract No. W-7405-ENG-36).

BACKGROUND OF THE INVENTION

The present invention relates generally to an apparatus and method for spectroscopic analysis, and more particularly to an apparatus and method for real-time generation and collection of fluorescence, reflection, scattering, and absorption information from a tissue sample to which multiple excitation wavelengths are sequentially applied.

Attempts at in situ real-time diagnostics for complex biological media, have been only marginally successful because of limitations in the spectroscopic techniques that are applicable. Conventional fluorescence spectroscopy is generally unable to resolve differences among similar biological tissue samples (or subtle differences in a given tissue sample) and has generally not proven reliable in detecting malignancy except with the aid of drugs such as hematoporphyrin derivatives which are used as targeting fluorescers (see, e.g., D. Kessel, "Tumor Localization And Photosensitization By Derivatives of Hematoporphyrin: A Review," IEEE J. Quantum Electron. QE-23, 1718 (1987)). This is because broad-band fluorescence from one group of chromophores can mask the emission from others, and if a different excitation wavelength is chosen to avoid that problem, other information is lost by the fact that only some types of the fluorescers are then excited. Recently researchers have demonstrated an improved technique for the fluorescence spectroscopy of tissue, called "fluorescence contour mapping" by some (see, e.g., R. Richards-Kortum et al., "Fluorescence Contour Mapping: Applications To Differentiation Of Normal And Pathological Human Tissues," Program of the Conference on Lasers and Electro-Optics 1989, 1989 Technical Digest Series 11, 140). In this technique, fluorescence spectra are obtained for many excitation wavelengths. The data are obtained using commercial instrumentation without fiber-optic transport of the light, and are presented in a two-dimensional (topographical) contour plot in which the fluorescence wavelength is plotted against the excitation wavelength for a series of intensity levels. This approach has proved capable of detecting subtle differences between healthy tissue and that exhibiting premalignancy changes. The principal disadvantages of the procedure, however, are that a single plot requires several hours of data gathering (thus eliminating its usefulness for real-time diagnostics) and that tissue is not examined in situ.

Excitation-Emission Matrix Fluorescence is a similar well-known technique from analytical chemistry for analyzing mixtures of organics. In its most usual form, this technique is slow, but precise. See, e.g., I. M. Warner, G. Patonay, and M. P. Thomas, "Multidimensional Luminescence Measurements," Analytical Chem. 57, 463A (1985), which reviews all fluorescence techniques used in analytical chemistry. A less precise, but rapid, form of Excitation-Emission Matrix Fluorescence has been developed. See, e.g., I. M. Warner, M. P. Fogarty, and D. C. Shelly, "Design Considerations For A Two-Dimensional Rapid Scanning Fluorimeter," Analytica Chemica Acta 109, 361 (1979) which is the pioneering work on dispersed-excitation-spot Excitation-Emission Matrix Fluorescence. This technique requires a large spot (several cm) containing a dispersed range of excitation wavelengths. Indeed, it is mentioned in the first Warner et al. reference that analysis speed can be obtained only at the cost of a large sampling area. Such large sampling areas are unsuitable for medical diagnostics because of the sub-mm-sc inhomogeneity of real biological samples. An apparatus for the Excitation-Emission Matrix Fluorescence analysis of remote samples, in which the excitation and emissions are delivered and gathered by means of optical fibers is described in J. B. Zung, R. L. Woodlee, M-R. S. Fuh, and I. M. Warner, "Recent Developments and Applications of Multidimensional Fluorescence Spectroscopy," SPIE 1054, Proceedings of Fluorescence Detection III (1989), p. 69; J. B. Zung, R. L. Woodlee, M-R. S. Fuh, and I. M. Warner, "Fiber Optic Based Multidimensional Fluorometer for Studies of Marine Pollutants," SPIE 990, Proceedings of Chemical, Biochemical, and Environmental Applications of Fibers (1988), p. 49; J. B. Zung, M-R. S. Fuh, and I. M. Warner, "Design and Characterization of a Fiber Optic-Based Fluorimeter," Anal. Chim. Acta 224, 235 (1989). Optical fibers are employed in an apparatus which has similarities with the present invention to access remote samples. These references teach the rejection of scattered radiation from samples by the light gathering apparatus, and in fact describe the deployment of the light delivery and light collection fibers in such a manner that scattering is minimized.

Single-excitation-wavelength fluorescence spectra are currently being widely studied for some specific analyses tissue partly as a result of increased interest in laser angioplasty (see, e.g., R. Richards-Kortum et al., "A Model For The Extraction Of Diagnostic Information From Laser Induced Fluorescence Spectra Of Human Artery Wall," Spectrochimica Acta 45A, 87 (1989). Other applications of single-spectrum analysis are illustrated in: R. M. Cothren et al., "Gastrointestinal Tissue Diagnosis By Laser-Induced Fluorescence Spectroscopy At Endoscopy," Gastrointestinal Endoscopy 36, 105 (1990); R. R. Alfano, A. Pradhan, G. C. Tang, and S. J. Wahl, "Optical Spectroscopic Diagnosis Of Cancer And Normal Breast Tissues," J. Opt. Soc. Am. B 6, 1015 (1989); and R. R. Alfano and M. A. Alfano, "Method For Detecting Cancerous Tissue Using Visible Native Luminescence," U.S. Pat. No. 4,930,516). Therein, the tissue to be examined is excited with a beam of monochromatic light, after a determination of the wavelength(s) at which maximum intensity of fluorescence occurs, and the fluorescence measured as a function of wavelength. A comparison of the spectrum of the excited tissues under investigation with the spectrum of known noncancerous tissue, allows the determination of the carcinomatoid status thereof, albeit with variable reliability. It is important to recognize that biological tissue is a form of matter unlike those (liquid, gas, or solid) normally encountered in analytical chemistry. With the exception of solid forms (bones, teeth, hair, etc.) tissue is usually composed of variously encapsulated liquids or semi-liquids. Not only is tissue inhomogeneous on a small scale, but it has a great deal of physical structure to it. Therefore, fluorescence measurement alone is an incomplete diagnostic for tissue. Fluorescence can reveal much about the chemical makeup of the tissue as a whole, but provides nothing about its structure. However, other optical properties of tissue such as reflection, absorption, and scattering may assist in more detailed analyses. Optical scattering (in which cellular structures divert the photon in a different direction without changing its energy) is very dependent on the tissue structure and, accordingly, quite sensitive to changes therein that accompany the development of cancer. It is usually such changes that a pathologist detects by eye when analyzing biopsy samples. The most sensitive and complete optical diagnostic for detecting the chemical and structural changes in the development of cancerous tissue would therefore be one that could detect all the possible optical responses of tissue.

Accordingly, it is an object of the present invention to provide an apparatus and method for real-time fluorescence analysis of tissue at multiple excitation wavelengths with a simultaneous measure of the absorption and scattering as a function of wavelength.

Another object of the invention is to provide an apparatus and method for identification of cancerous tissue either in vitro or in vivo in real time with high reliability.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the apparatus hereof for recording spectroscopic information from a tissue sample in real time includes, in combination, a pulsed wavelength-tunable light source for rapidly generating light having a chosen range of wavelengths, fiber optics for collecting the light generated from the light source and for directing the light onto the sample, fiber optics for collecting the light emitted from and scattered from transmitted through the sample as a result of the interaction of the sample with the incident light thereon, and for directing this light into a detector, and a detector for receiving the light from the collection fiber optics and for rapidly detecting substantially all wavelengths of the collected light; whereby the optical response of the sample to the incident wavelengths of radiation are observed over substantially all wavelengths emitted therefrom within three seconds.

In a further aspect of the present invention, in accordance with its objects and purposes, the method hereof for recording spectroscopic information from a tissue sample in real time includes the steps of rapidly generating multiple pulsed wavelengths of light, collecting and directing the light onto the sample under investigation, and collecting and rapidly detecting substantially all wavelengths of light emitted and scattered from the sample as a result of the interaction thereof with the incident light; whereby the spectroscopic response of the sample to the incident wavelengths of radiation is observed over substantially all wavelengths emitted therefrom within three seconds.

Benefits and advantages of the invention include the noninvasive, real-time optical analysis of tissue samples which will allow the detection of malignancies with high reliability.

BRIEF DESCRIPTION OF THE DRAWINGS

The accompanying drawing, which is incorporated in and forms a part of the specification, illustrates one embodiment of the present invention and, together with the description, serves to explain the principles of the invention.

DETAILED DESCRIPTION OF A PREFERRED EMBODIMENT OF THE INVENTION

Briefly, the present invention includes a pulsed-light-source fiber-optic based, noninvasive, real-time optical analysis apparatus having applications in medicine and other fields where rapid identification of a biological substance is required. The system includes four major subsystems: 1) a rapidly tunable pulsed-excitation light source, 2) a fiber-optic delivery/collection system, 3) a light detection system where multiple wavelengths are simultaneously detected, and 4) a computer for data acquisition and analysis. It should be mentioned that subtle differences in the plots of emitted light versus excitation wavelength for similar samples can often be recognized by simply observing two such plots together using the unaided eye.

Figure 1:
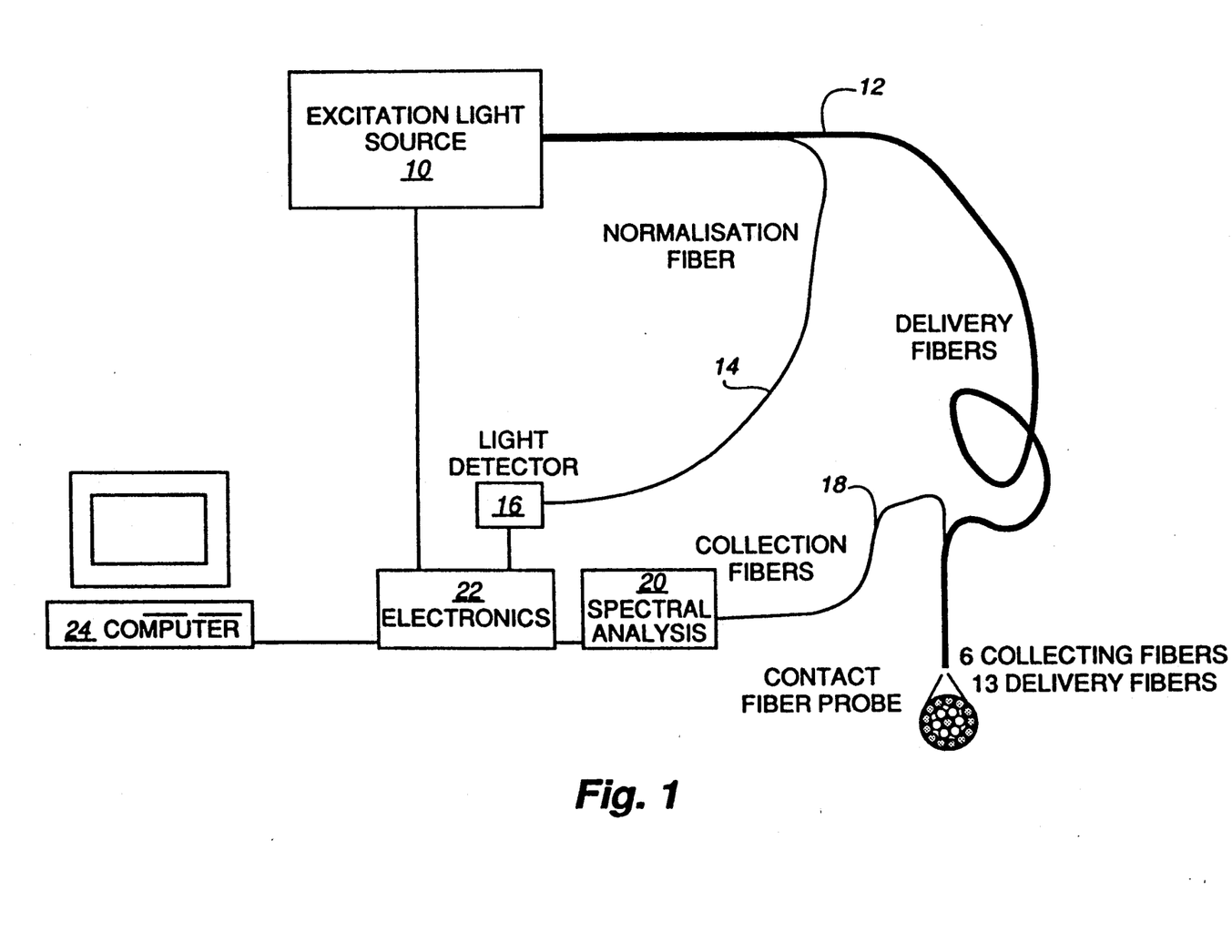
FIG. 1 shows a schematic representation of a generalized embodiment of the apparatus of the present invention illustrating, in particular, the construction of a typical optical fiber light delivery and collection system.
Figure 2:
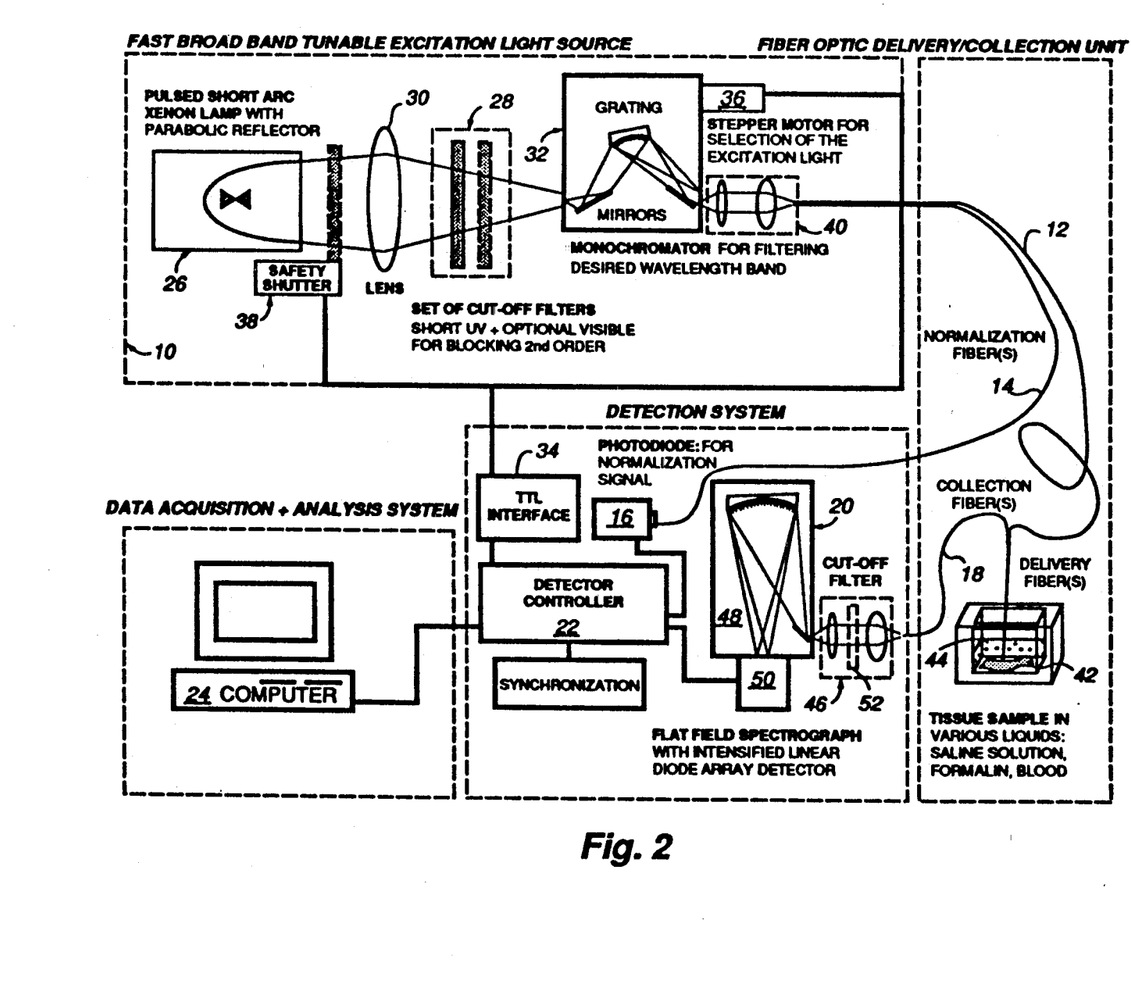
FIG. 2 shows a schematic representation of one embodiment of the apparatus of the present invention illustrating the use of a pulsed xenon arc lamp combined with a monochromator as a tunable light source.

Reference will now be made in detail to the present preferred embodiment of the invention, an example of which is illustrated in FIGS. 1 and 2. Similar or identical structures or components are identified by the same call-out numbers. Figure shows a schematic representation of a generalized embodiment of the apparatus of the present invention, illustrating, in particular, the construction of a typical optical-fiber light delivery and collection system, and one of many possible fiber-optic probe configurations. Light generated from rapidly tunable, pulsed light excitation source, 10, is coupled into at least one optical fiber, 12, for direction onto the sample under investigation (not shown). It is necessary that the light source be pulsed because the short exposure time at each excitation wavelength, when the complete sequence is generated in real-time, precludes the use of any practicable non-laser, continuous-wave light source, such as a cw arc lamp of reasonable power (as used by Zung et al.). Note that current lasers have such limited tuning capability that arc lamps appear to be the only viable light source. Only a pulsed source, such as a pulsed arc lamp, can introduce sufficient photons into the sample during reasonable irradiation periods to generate measured light levels having usable signal-to-noise ratios. In addition, the short exposure time of the pulsed source makes it possible to correspondingly shorten the exposure time of the light detectors. Since the background noise in virtually all light detectors integrates during the detector's exposure time, a short "on" time minimizes the collected noise and improves the signal-to-noise ratio of the measurement system. A portion of the generated light is coupled into at least one additional optical fiber, 14, and directed to a detector, 16, for the purpose of output normalization as a function of wavelength. At least one optical fiber, 18, collects light emitted from the excited sample upon interaction with the light from the excitation light source. The collected light includes reflected, transmitted, and scattered light, as well as fluoresence from the sample. It should be mentioned that the use of separate optical fibers for light collection from those used for directing the light onto the sample permits collected light to include excitation wavelengths as well as other wavelengths. Moreover, if the excitation and collection fibers are brought together in a substantially parallel manner in the vicinity of the sample to form a probe, and the ends thereof placed in contact with the tissue sample under investigation, transmitted light reaching the collection fibers must actually pass through the sample. Only in this way can the complete optical response of the tissue be observed, and information reflecting the state of the material be recorded. Spectrum analyzer 20 receives the collected light from optical fiber 18 and simultaneously analyzes all chosen wavelengths providing intensity versus wavelength information to a data acquisition system 22, which may include a computer 24 for data acquisition, comparisons, display purposes, and diagnostic evaluations.

FIG. 2 shows a schematic representation of one embodiment of the apparatus of the present invention illustrating the use of a pulsed xenon arc lamp combined with a monochromator as a tunable light source. In general, it would be desirable for light sources to be tunable from 250 nm to 1100 nm with an adjustable bandwidth of 1–20 nm, optimized for efficient fiber coupling and fast scanning (up to 1000 different excitation wavelengths/sec). Brightness (watts/steradian) must be high to allow for effective coupling into an optical fiber. A xenon arc lamp must be pulsed to meet the high-brightness requirement. Optical sources that can be used include the following: 1) multiple-wavelength lasers, such as mixed-gas (argon and krypton) ion lasers, dye or multiple-dye lasers (pumped by either flashlamp or laser), 2) an optical parametric oscillator (OPO) that is pumped by any uv laser, such as a frequency-quadrupled Nd:YAG laser, and 3) pulsed xenon short-arc lamp in cooperation with a rapidly tunable optical filter, such as a small monochromator or a set of interference filters. Rapid tunability can be achieved with a tuning element, such as grating, prism, mirror, or nonlinear crystal, whose angle or position is changed by a servo-motor, piezoelectric driver or galvanometer. The primary light source used for the collection of the data shown in FIGS. 3–5 hereof was a commercially available pulsed xenon short-arc lamp, 26, which incorporates an aluminum-coated ceramic parabolic reflector. This source provides broad-band light output (from 250 to 1100 nm) from a small (approximately 1 mm) arc. The shortest wavelengths were blocked by 280 nm cut-off filters, 28. The transmitted broad-band light (290–100 nm) was focused using a quartz lens, 30, to the input slit (1 mm) of monochromator, 32, which provides rapidly tunable filtering (in first or higher order) or white light (in zero order). The position of the monochromator grating determined the actual wavelength selection and was controlled by a TTL pulse-interfaced stepper motor, 34, 36. For excitation wavelengths longer than 500 nm, a second cut-off filter could be placed in the light path (in front of the monochromator entrance slit) to suppress the second order of the uv blue light which overlaps the green-red light at the exit slit of the monochromator. The stepper-motor-controlled grating had a resolution of 0.25 nm. A 10-nm increment in the excitation wavelength was generated by the stepper motor in less than 0.03 second. A manually-controlled safety shutter, 38, may be included to prevent accidental exposure of the sample of optics to the light of the arc lamp. The light exiting the monochromator was imaged through an optional numerical aperture-matching lens system, 40, to optical fibers 12 and 14. The actual bandwidth of the excitation light was determined by the dimensions of the entrance and exit slits as well as that for the collection fiber. Typically, the fiber size governs the band-pass in the same manner as an exit slit. For example, a 0.1-mm entrance slit with a linear array of 200-um collection fibers results in a 4–5 nm excitation source bandwidth in first order of the grating. Note that due to the finite size of the arc in the xenon lamp, and its relatively large beam divergence (approximately 4°–5°), the minimum achievable spot size at the fiber tips is in the range of 1–3 mm. Therefore, the smaller the pickup fiber diameter, the less light can be collected by a single fiber.

While various fiber-optic delivery/collection systems were investigated, the completed demonstration system incorporates one of the more simple examples. This system was comprised, as shown in FIG. 1 hereof, of three separate optical-fiber bundles. The ends of one fiber-bundle pair are disposed spatially adjacent at the monochromator end and a different pair (derived from one of the first pair added to a third fiber bundle) at the tissue end. Each of the two fiber-bundle pairs has one fiber bundle in common. The common fiber bundle delivers the excitation light from the monochromator to the tissue sample 42 shown in FIG. 2 hereof, where the light is partially reflected (due to index mismatch and scattering in the tissue) and partially scattered and absorbed. The second (normalization) fiber bundle, 14, at the monochromator end delivers excitation light to photodiode, 16, allowing the system to keep track of the pulse-to-pulse (and wavelength-to-wavelength) variations in the light delivered to the tissue. The first (delivery) fiber bundle, 12, and the third (collection) fiber bundle, 18, are combined parallel at the tissue end. A fraction of the absorbed photons is converted into detectable fluorescence photons. The collection fiber bundle collects reflected, scattered, and frequency-shifted (fluorescence) light, delivering it to a spectrograph.

Light collection is optimized by matching the numerical apertures of the fiber bundles to the acceptance angle of the spectrograph. The index mismatch at the tissue end can be significantly decreased if the fiber end is immersed in a liquid, 44. For example, saline solution and formalin (used for preserving tissue samples) have good optical properties for such purpose. However, blood modifies the signal through absorption as a function of the fiber bundle tip distance from the tissue. Moreover, the optical signal delivered to the spectrometer depends on the distance of the fiber-bundle end from the tissue, as well as on the geometry of the fiber tip design. Changing this distance has two effects on the signal. The most evident is the approximately $r^{-4}$ dependence of the light-collection efficiency of the fiber, resulting in more collected light at closer proximity. Variations in fiber geometries, combined with the scattering and reabsorption of fluorescent light in most biological tissues, are the primary cause of the irreproducibility of bio-fluorescence data published in the literature. Therefore, the preferred sampling mode is achieved with the optical-fiber bundle probe in contact with the sample.

The fiber bundles can be guided to the diagnosis site by a variety of methods. For example, in medicine, endoscopic delivery, catheter delivery, and hypodermic delivery may all be readily employed.

A detection system which records and digitizes both the fluorescence and the amount of light incident on the sample tissue, and transfers the data to the host computer system for additional analysis was employed. The spectrum of the scattered and fluorescence light collected from the tissue for each excitation wavelength by optical fiber 18 was coupled by an optional lens system 46 into a flat-field spectrograph, 48, where it was dispersed, and light intensities as a function of wavelength were recorded using a multichannel detector, 50, such as an intensified linear diode array. A charge-coupled detector array could also be used. This combination allows fast recording of the whole spectrum, for example, 300–900 nm, for each excitation pulse. In some instances a cut-off filter, 52, was used to suppress the second order of the grating. The linear diode array was interfaced to the detector controller, 22, which serves as a buffer to the computer, 24. The same controller also integrated the signal from photodiode, 16, over the exposure time of the diode array, producing a number proportional to the total number of photons used for excitation of the tissue fluorescence. The total exposure at each wavelength can thus be measured by the reference photodiode, coupled to the detector/controller and then used by the host computer to normalize the data for variations in the light source with wavelength and also for the wavelength dependence of the monochromator efficiency. TTL pulse forms are employed for control of the stepper motor of the monochromator, monochromator position signal, etc. A custom-designed TTL interface allowed synchronization of the data acquisition with the rest of the hardware.

The data acquisition system controlled both the excitation light source and detection system through a self-learning feedback loop. The data acquisition mode is thus automatically self-adjusting (optimum signal-to-noise) to the sample characteristics. Data were also corrected for variations in the excitation light and the overall spectral response of the detection system.

There are a variety of ways that the data can be analyzed for interpretation, but a preferred analysis begins with normalizing each spectrum. Then all spectra were corrected for the wavelength response of the collection system, and the backscattered component of the excitation source (which contains the structure information) might be digitally subtracted from each. For graphic representation, the data could be displayed in a manner similar to a topographic map, excitation wavelength being plotted against signal wavelength and amplitudes being shown as planes of constant intensity. Colors or shades of grey can be used to represent different intensity levels. Another form of data plot is a psuedo-three-dimensional representation. This is the method used in FIGS. 3 and 4.

Figure 3:
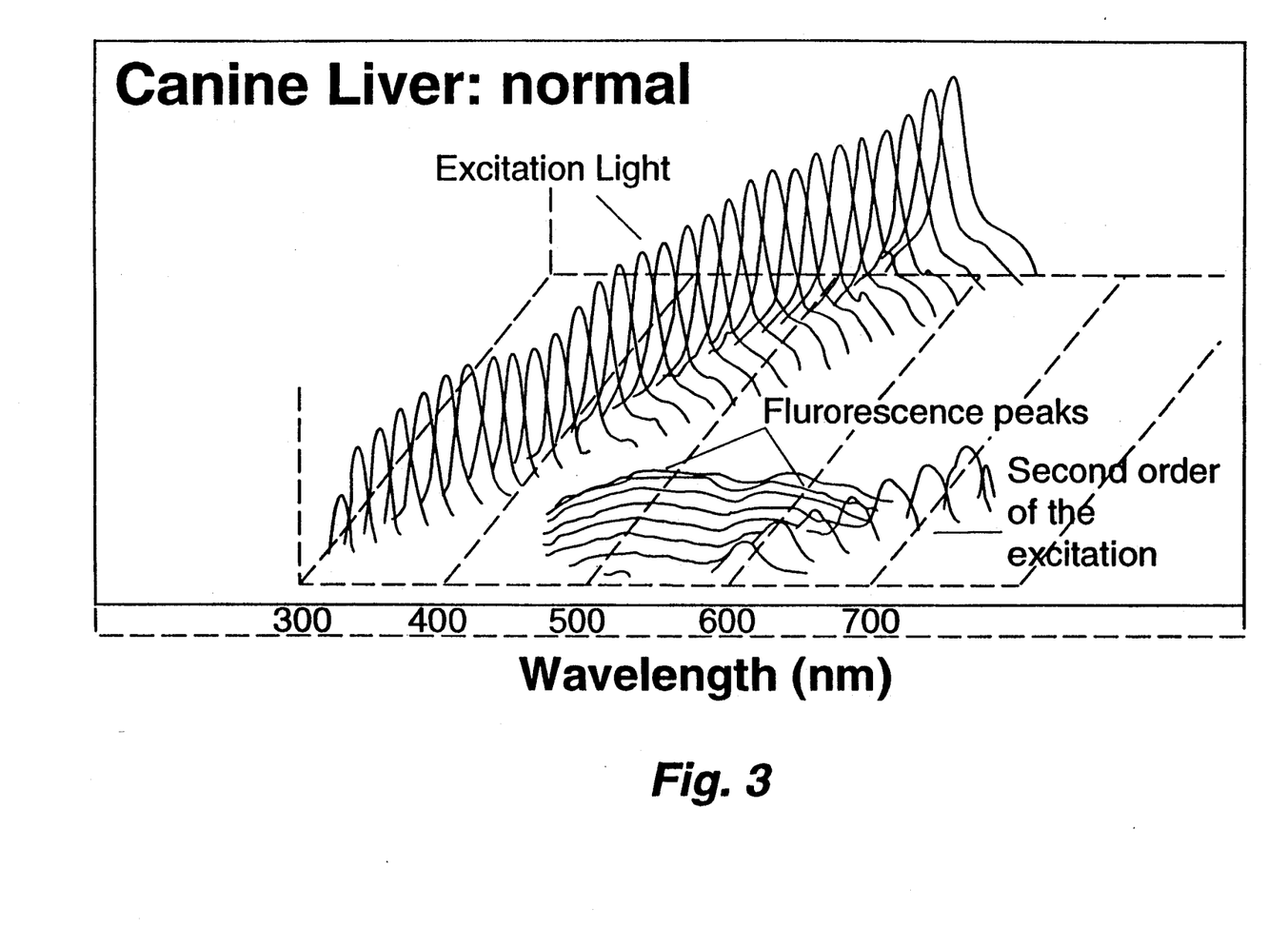
FIG. 3 shows a plot of the normalized intensity of collected light from a liver sample where no abnormality is suspected, versus the excitation frequency, the normalized intensity at every point being divided by an average of similar plots taken from a normal liver.
Figure 4:
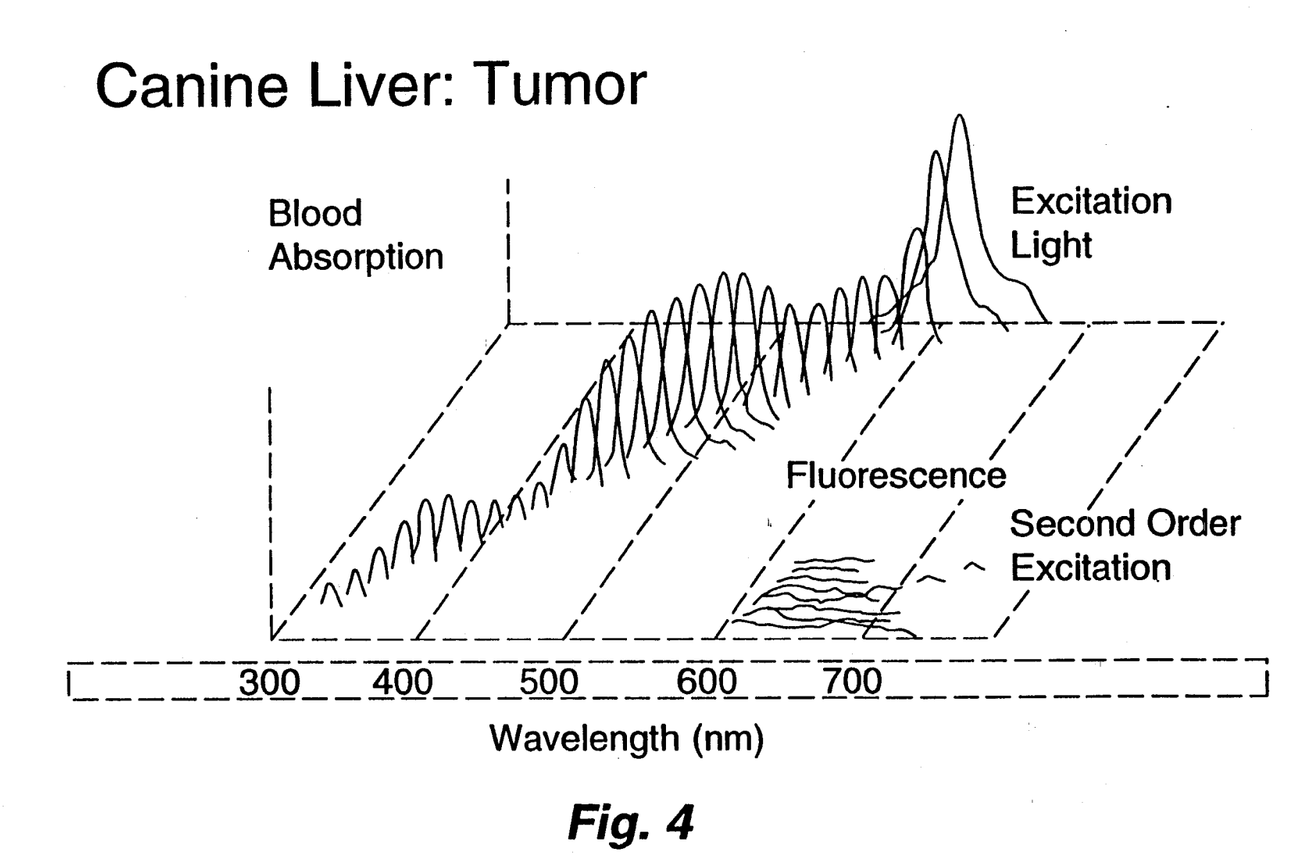
FIG. 4 shows a plot of the normalized intensity of emitted light from a liver sample having a tumor, versus the excitation frequency, the normalized intensity at every point being divided by an average of similar plots taken from a normal liver.

Interpretation of the data may also include comparison of the signatures against a library of known signatures. Parameters such as peak locations or the ratio of the "left-right" gradient of a feature to its "up-down" gradient (among a large variety of parameters that are available, can provide unique signature designations that are not available from conventional fluorescence spectroscopy. Typical results are shown in FIGS. 3 and 4 hereof. FIG. 3 shows a plot of the normalized intensity of emitted light from a liver sample where no abnormality is suspected, versus the excitation and emission frequencies FIG. 4 shows a similar plot of the normalized intensity of emitted light from a liver sample having a tumor. In both of these figures the right-handmost peaks are artifacts of the grating in he spectrometer. The differences in optical signature from the tumorous tissue are significant; not only is the fluorescence lower in intensity and shifted to longer wavelengths, but there are new strong absorptions. This measurement was derived from a tumor that was obvious to the eye from its color.

Figure 5:
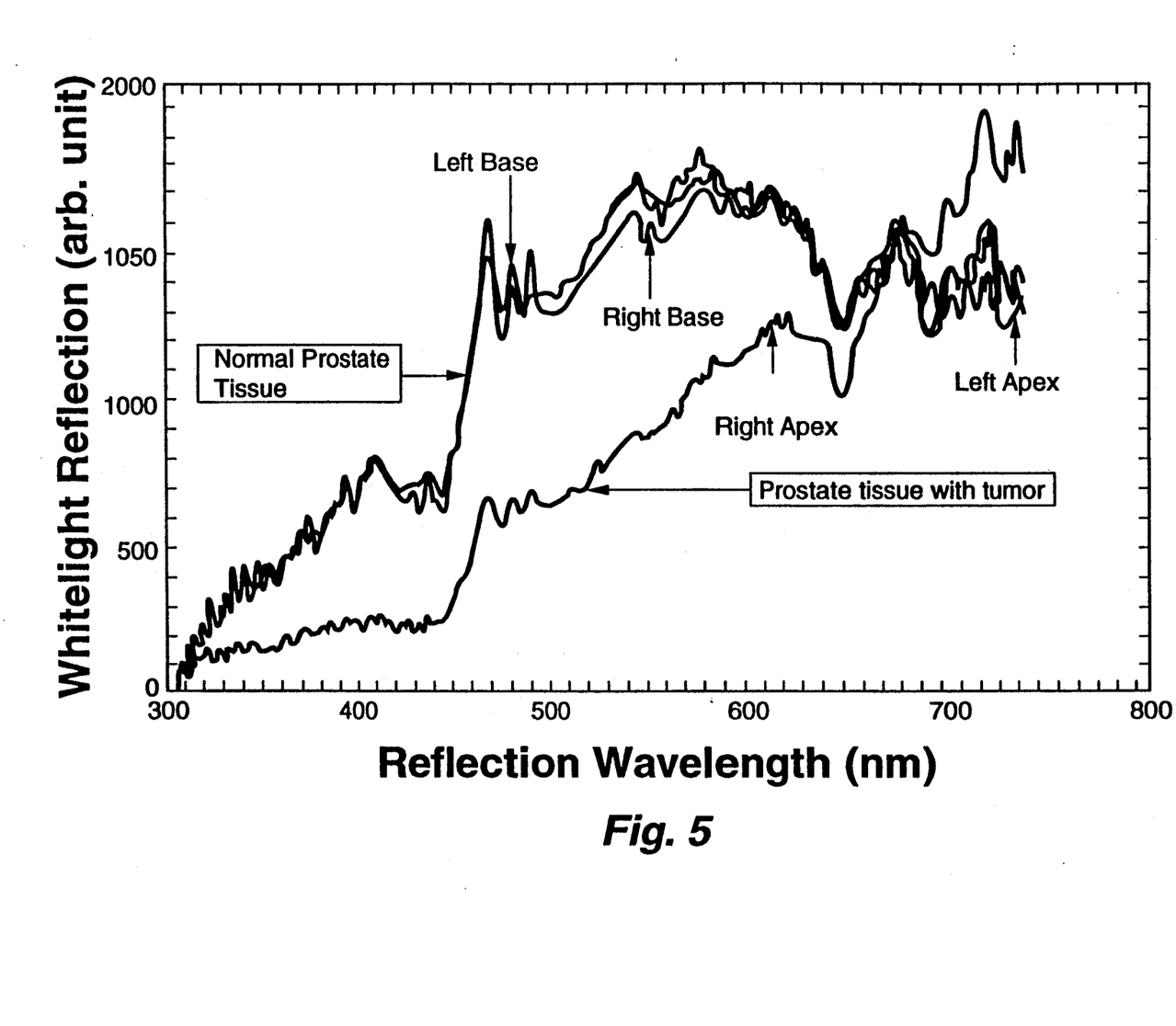
FIG. 5 shows four plots of intensity as a function of collected light wavelength for four locations on a surgically removed human prostate gland which was illuminated by white light.

Additionally, when the detection monochromator is operated in the zero order, one can obtain a different scattering/absorption spectrum. This data may be used for a good-guess estimate of the ideal exposure times, or it may be plotted and used as an additional diagnostic. This is illustrated in FIG. 5 hereof. FIG. 5 shows four plots of intensity as a function of collected wavelength for four locations on a surgically removed human prostate gland which was illuminated by the zero order white light. Subsequent pathological examination of the same four sites uncovered malignancy only in the right apex, in agreement with the spectroscopic determination. The profound difference between the light reflected from normal tissue and that reflected from tissue containing cancerous growth is apparent from the Figure. This result is more indicative of the potential of the present invention, since in this case the four sites sampled were identical to the unaided eye.

The present apparatus may be used for analysis in the following environments:

(1) the identification of unknown tissue in vitro, (2) the identification of unknown tissue in vivo, (3) the detection of subtle tissue changes as a function of location in vitro, and (4) the detection of subtle tissue changes as a function of location of vivo and in real time.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application, thereby enabling others skilled in the art to best utilize the invention in various embodiments and with 5 various modifications as are suited to the particular use contemplated. It is intended that the scope of the invention be defined by the claims appended hereto.

What we claim is:

1. An apparatus for recording the optical responses of biological tissue, comprising in combination:
   a. wavelength-tunable light generation means for rapidly generating high-brightness multiple wavelengths of light within a chosen range of wavelengths;
   b. fiber-optic means for collecting the light generated from said light generation means and for directing the light into a small volume of the biological tissue under investigation;
   c. detection means for receiving and for rapidly detecting light; and
   d. fiber-optic means for collecting the light emitted and scattered from the biological tissue and for directing the emitted and scattered light into said detection means, said means for collecting the generated light and said fiber-optic means for collecting the emitted and scattered light being disposed in a substantially parallel manner in the proximity of one another and in contact with the biological tissue, whereby light emitted, transmitted and scattered by the biological tissue is measured.

2. The apparatus as described in claim 1, further comprising light intensity sampling means for determining the output intensity of said light generation means at every wavelength generated thereby.

3. The apparatus as described in claim 1, wherein said light generation means comprises a pulsed xenon arc lamp in cooperation with a rapidly tunable monochromator.

4. The apparatus as described in claim 1, wherein said light generation means comprises a tunable, laser-driven nonlinear optical oscillator.

5. The apparatus as described in claim 1, wherein said light generation means includes laser means.

6. A method for recording spectroscopic information from a sample, comprising the steps of:
   a. rapidly generating high-brightness multiple wavelengths of light within a chosen range of wavelengths;
   b. collecting the generated light and directing the light into a small volume of the sample under investigation; and
   c. collecting and rapidly detecting substantially all wavelengths of light emitted and scattered at the surface of the small volume emerging from the sample in the opposite direction from the incident light resulting from the interaction of the sample with the light incident thereon; whereby light emitted, scattered, and transmitted by the sample in response to the incident wavelengths of radiation is observed.

7. The method as described in claim 6, further comprising the step of determining the output intensity of light generated at every wavelength generated in said step of light generation.

* * * * *